(12) United States Patent
Garcia et al.

(10) Patent No.: US 7,766,886 B2
(45) Date of Patent: Aug. 3, 2010

(54) DRAINAGE DEVICES AND METHODS

(75) Inventors: Maurice M. Garcia, San Francisco, CA (US); Marshall L. Stoller, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 727 days.

(21) Appl. No.: 11/193,304

(22) Filed: Jul. 30, 2005

(65) Prior Publication Data

US 2007/0027433 A1 Feb. 1, 2007

(51) Int. Cl.
*A61M 1/00* (2006.01)
(52) U.S. Cl. .................... 604/323; 604/324; 604/319
(58) Field of Classification Search .............. 604/540, 604/541, 543, 290, 73, 320, 319, 323, 6.15; 251/264
See application file for complete search history.

(56) References Cited

U.S. PATENT DOCUMENTS

| | | | | |
|---|---|---|---|---|
| 3,463,159 A * | 8/1969 | Heimlich | .................. | 604/247 |
| 3,635,380 A * | 1/1972 | Fitzgerald | .................. | 222/484 |
| 3,941,149 A * | 3/1976 | Mittleman | .................. | 137/493.1 |
| 3,945,392 A * | 3/1976 | Deaton et al. | .................. | 137/205 |
| 3,967,645 A * | 7/1976 | Gregory | .................. | 137/846 |
| 4,392,858 A * | 7/1983 | George et al. | .................. | 604/133 |
| 4,430,073 A * | 2/1984 | Bemis et al. | .................. | 604/119 |
| 4,493,701 A * | 1/1985 | Bootman et al. | .................. | 604/73 |
| 4,664,660 A * | 5/1987 | Goldberg et al. | .................. | 604/321 |
| 4,738,672 A * | 4/1988 | Malette | .................. | 604/319 |
| 4,828,546 A | 5/1989 | McNeil et al. | | |
| 4,828,552 A * | 5/1989 | Malette | .................. | 604/319 |
| 4,990,137 A | 2/1991 | Graham | | |
| 5,019,059 A | 5/1991 | Goldberg et al. | | |
| 5,045,077 A * | 9/1991 | Blake, III | .................. | 604/321 |
| 5,112,301 A * | 5/1992 | Fenton et al. | .................. | 604/30 |
| 5,290,263 A * | 3/1994 | Wigness et al. | .................. | 604/247 |
| 5,401,255 A * | 3/1995 | Sutherland et al. | .................. | 604/247 |
| 5,439,022 A * | 8/1995 | Summers et al. | .................. | 137/102 |
| 5,505,717 A | 4/1996 | Moore | | |
| 5,549,584 A | 8/1996 | Gross | | |
| 5,843,171 A * | 12/1998 | Campbell et al. | .................. | 606/198 |
| 6,059,745 A * | 5/2000 | Gelbfish | .................. | 604/6.09 |
| 6,554,805 B2 * | 4/2003 | Hiejima | .................. | 604/247 |
| 6,575,960 B2 * | 6/2003 | Becker et al. | .................. | 604/533 |
| 7,422,034 B2 * | 9/2008 | Dahm | .................. | 137/846 |
| 7,533,696 B2 * | 5/2009 | Paul, Jr. | .................. | 137/846 |
| 2003/0098430 A1 * | 5/2003 | Leinsing et al. | .................. | 251/149.6 |

(Continued)

OTHER PUBLICATIONS

BD Medical Systems Product Brochure. "BD Bard-Parker Heimlich Chest Drain Valve" [online]. Jan. 2002, [Retrieved on Oct. 17, 2005] <URL: http://www.bd.com>.

*Primary Examiner*—Tatyana Zalukaeva
*Assistant Examiner*—Susan Su
(74) *Attorney, Agent, or Firm*—Townsend and Townsend and Crew LLP

(57) ABSTRACT

Active and passive wound drainage systems and method are provided. A drainage device includes an input passage for receiving the fluid from a site on or within the patient's body, a container for holding the fluid, and a reversible valve disposed between the input passage and the container. The reversible valve in an original configuration provides unidirectional fluid flow from the input passage toward the container, and in a reversed configuration provides fluid flow from the container toward the input passage.

10 Claims, 7 Drawing Sheets

U.S. PATENT DOCUMENTS

| | | | |
|---|---|---|---|
| 2003/0171721 A1* | 9/2003 | Enomoto et al. | 604/247 |
| 2003/0195472 A1* | 10/2003 | Green et al. | 604/167.04 |
| 2004/0176739 A1* | 9/2004 | Stephens et al. | 604/523 |
| 2005/0256461 A1* | 11/2005 | DiFiore et al. | 604/247 |
| 2006/0041189 A1* | 2/2006 | Vancaillie | 600/154 |
| 2006/0142735 A1* | 6/2006 | Whitley | 604/537 |
| 2007/0056647 A1* | 3/2007 | Frayne | 137/843 |
| 2007/0246680 A1* | 10/2007 | Chao | 251/340 |

* cited by examiner

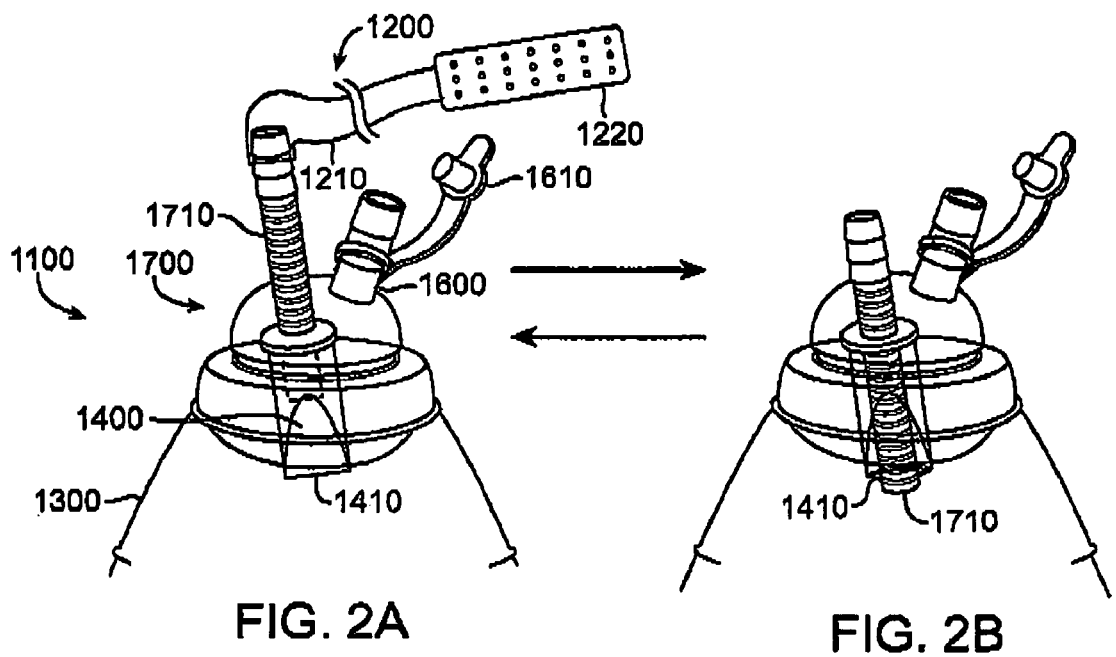
FIG. 2A
FIG. 2B
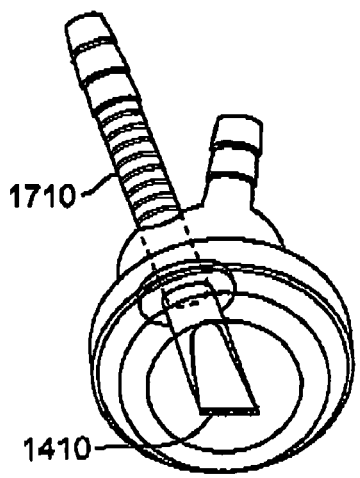
FIG. 2C
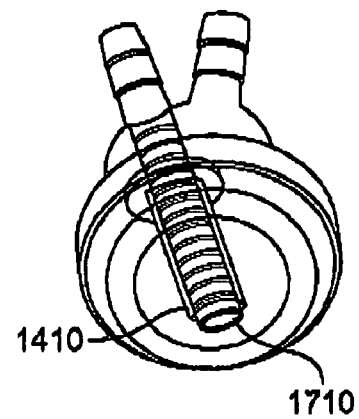
FIG. 2D

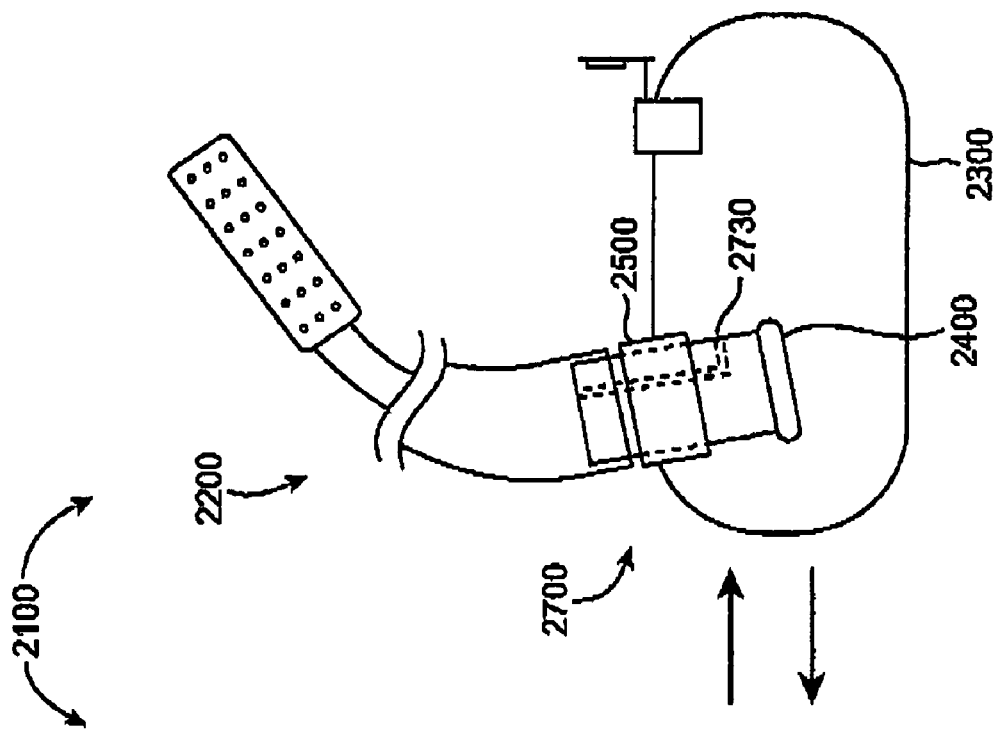
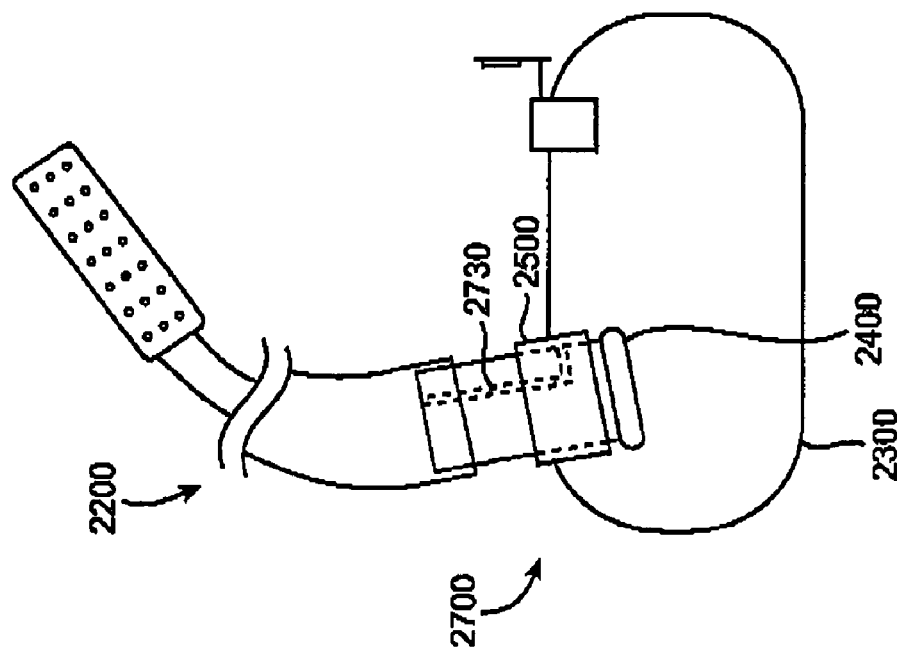

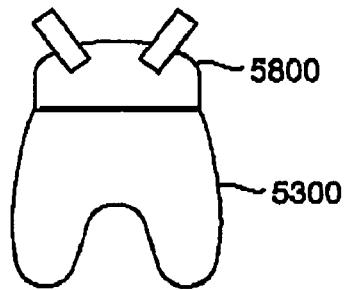
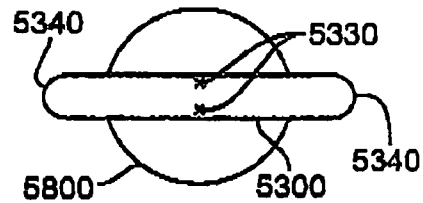
FIG. 7A  FIG. 7B
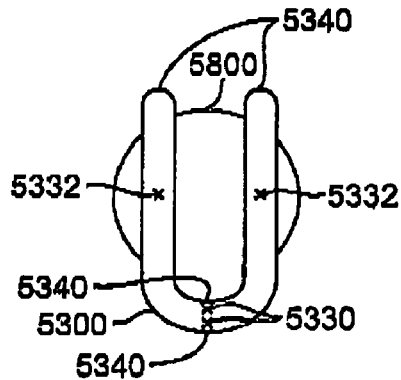
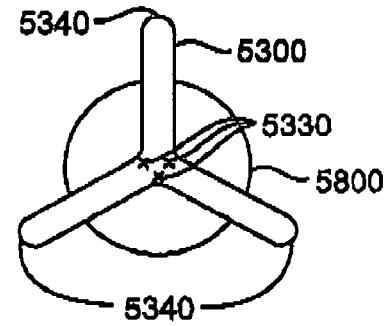
FIG. 7C  FIG. 7D
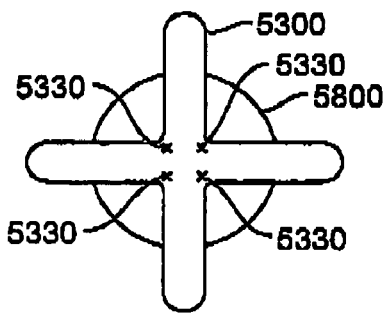
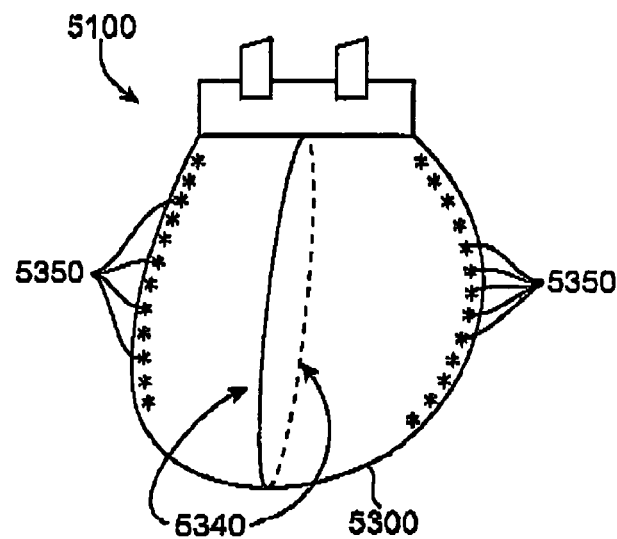
FIG. 7E  FIG. 7F

DRAINAGE DEVICES AND METHODS

CROSS-REFERENCES TO RELATED APPLICATIONS

NOT APPLICABLE

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

This invention relates to the field of medical suction devices, and in particular to suction wound drains.

Closed suction drains are ubiquitously used in medical practice to suction and collect fluid and other material from surgical wounds. For example, surgical wounds frequently benefit from drainage during the post operative period. This can involve removing fluid which is naturally expressed from the wounds, characterizing and measuring drained fluids, and monitoring the operative site for unexpected or undesired leakage of fluids. Hence, the drains are effective in promoting healing and recovery, while minimizing the likelihood of infection. Known closed suction wound treatment devices, such as Jackson-Pratt evacuator drain systems, typically include a small plastic semi-spherical or football-shaped bulb which supplies suction to a drainage tube that the surgeon leaves within the patient's wound. This suction bulb, which is connected to the drainage tube via a one-way Heimlich valve, also serves as a collection reservoir for fluid drained from the wound. When removing such surgical drains from the patient, one simply pulls the drain from the patient's wound.

Despite the wide use of these closed-system wound drain devices, their suction characteristics remain poorly understood. For example, one common assumption is that releasing suction within the bulb also releases suction at the drain end of the drainage tube. The present inventors have discovered through clinical observations, however, that suction is not released at the drain element after release of the bulb section, as previously thought. What is more, many current approaches do not provide a mechanism whereby an active drainage system can be efficiently converted to a passive drainage system. Again, the present inventors have discovered that passive drainage is not simply achieved by release of the bulb section.

In light of the above unexpected limitations of traditional closed-system suction wound drains, what is needed are drainage devices and methods to optimize drainage function by providing easy and safe dissipation of the negative suction prior to removing the drain from the patient. What is also needed are devices and methods that provide safe and efficient transformation from an active drainage system to a passive drainage system. What is further needed are calibrated suction bulbs for applying a controlled vacuum to a wound site. The present invention provides such solutions.

BRIEF SUMMARY OF THE INVENTION

The present invention provides drainage devices and methods that are safe, effective, and useful for minimizing pain the pain experienced by the patient. Advantageously, the present invention provides techniques whereby negative pressure at or within a surgical drainage tube can be efficiently released when desired, so that the a drain can be removed from the patient without pulling local or entrapped tissues upon withdrawal, or without otherwise inducing tissue trauma or hemorrhage. These approaches are particularly in ensuring that a drainage device is truly off suction when unplugging a bulb drainage port prior to removal of the closed suction drain.

The present invention provides a closed system approach for draining wounds. There is no need to cut or disconnect tubing, and a reversible suction valve provides dual action active (e.g suction) and passive (e.g. gravity) drainage modes. Bulb designs according to the present invention provide controllable amounts of suction, varying from low suction to high suction. The present invention also provides an optional closed-system passive drainage mode, and further provides a clean, spill-save method to release drain suction.

In a first aspect the present invention provides a drainage device for drawing fluid from a patient. The device can include an input passage for receiving the fluid from a site on or within the patient's body, a container for holding the fluid, and a reversible valve disposed between the input passage and the container. The reversible valve in an original configuration can provide unidirectional fluid flow from the input passage toward the container, and in a reversed configuration provide fluid flow from the container toward the input passage. In some aspects, the reversible valve includes a one-way Heimlich valve in cooperative association with a stent such that when the reversible valve is in the original configuration, fluid flow from the input passage toward the container forces a seal of the Heimlich valve to an open position and fluid flow from the container toward the input passage forces the seal of the Heimlich valve to a closed position, and when the reversible valve is in the reversed configuration, the stent is disposed through the seal to maintain the seal in the open position. In related aspects, the reversible valve includes a one way Heimlich valve in cooperative association with a bypass, such that when the reversible valve is in an original configuration the one-way valve provides for unidirectional fluid flow from the output passage toward the container, and in a reversed configuration the bypass is engaged with the one-way valve to as to provide fluid flow from the container toward the input passage via the bypass.

In some aspects, the drainage device also includes a sealable port coupled with the container. In other aspects, the drainage device includes a vent coupled with the container, where the vent provides unidirectional fluid flow through a venting port out of the container. The vent can include a diaphragm valve or a Heimlich valve, or any other type of valve, including any of a variety of one-way valves. In related aspects, the device further includes a shell that houses the container. The shell can include an aperture for receiving a drainage tube of the input passage therethrough.

In another aspect, the present invention provides a method of drawing a fluid from a patient. The method can include placing an input passage at a site on or within the patient's body, such that the input passage is coupled with a container via a reversible valve. The method can also include disposing the reversible valve in a first configuration that provides unidirectional fluid flow from the input passage toward the container, setting the pressure in the container to a first negative pressure, and setting the pressure in the input passage to a second negative pressure such that the first negative pressure is less than the second negative pressure. The method can also include allowing the fluid to flow from the site on or within the patient's body into the container via the input passage and the reversible valve, and after allowing the fluid to flow into the container, setting the pressure in the container and the input passage to atmospheric pressure and removing the input passage from the patient. In some aspects, setting the pressure in the container to a first negative pressure can include detaching a plug from a venting port of the container, applying a compression force to the container to expel fluid from the container through the venting port, reattaching the plug with the venting port, and releasing the compression force from the container. In related aspects, setting the pressure in the container and the input passage to atmospheric pressure can include detaching a plug from a venting port of the container, and disposing the reversible valve in a second configuration that provides fluid flow from the container toward the input passage. In still further related aspects, disposing the reversible valve in a second configuration can include compromising a one-way valve of the reversible valve. Compromising the one-way valve of the reversible valve can include stenting the one-way valve. In related aspects, compromising the one-way valve of the reversible valve can include bypassing the one-way valve. The method of drawing fluid from a patient can also include expelling air from the container via a vent in the container when the reversible valve is in the first configuration. Further, expelling air from the container can include squeezing the container.

In another aspect, the present invention provides a method of drawing a fluid from a patient, where the method includes placing an input passage at a site on or within the patient's body, the input passage coupled with a container via a one-way valve that allows fluid flow from the input passage toward the container, compromising the one-way valve such that is allows fluid flow from the container toward the input passage, allowing the fluid to flow from the site on or within the patient's body into the container via the input passage and the compromised one-way valve, and allowing air to flow out of the container via a vent. In some aspects compromising the one-way valve includes stenting the one-way valve. In other aspects, compromising the one-way valve includes bypassing the one-way valve. The one-way valve can be a diaphragm valve, a Heimlich valve, or any other type of one-way valve. In related aspects, the device further includes a shell that houses the container. The shell can include an aperture for receiving the input passage therethrough.

For a fuller understanding of the nature and advantages of the present invention, reference should be had to the ensuing detailed description taken in conjunction with the accompanying drawings.

BRIEF DESCRIPTION OF THE DRAWINGS

FIGS. 2A-D show a wound drainage system according to one embodiment of the present invention.

FIGS. 4A and 4B illustrate a wound drainage system according to one embodiment of the present invention.

FIGS. 7A-F illustrate wound drainage systems according to various embodiments of the present invention.

DETAILED DESCRIPTION OF THE INVENTION

Figure 1:
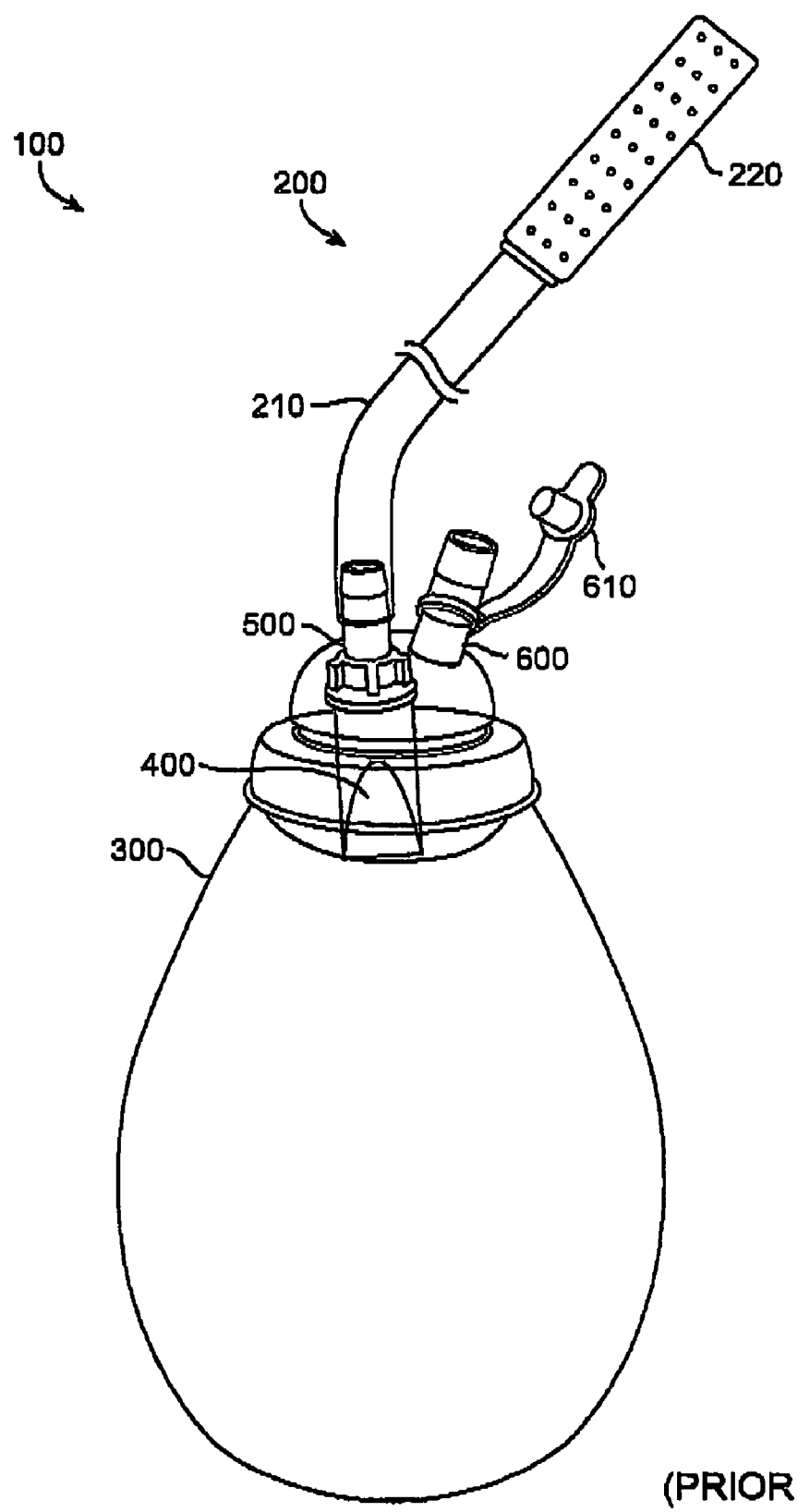
FIG. 1 shows a known wound drainage system.

Turning now to the drawings, FIG. 1 illustrates a currently known drainage device 100 such as a closed system drainage suction device, which includes an input passage 200 having a drainage tube 210 and a drain 220. Drainage device 100 also includes a container 300, a one-way valve 400, a valve port 500, and a venting port 600 having a plug 610. As shown here, suction bulb reservoir or container 300 often has two ports 500 and 600. Venting port 600 is typically a tube-shaped lumen which connects the inside of container 300 to the outside. Venting port 600 can be plugged or unplugged with an attached plug 610. Valve port 500 can also be a tube-shaped lumen, across which lies one-way valve 400, which in many cases is a Heimlich valve. One-way valve 400 is oriented to allow one-way flow of fluid toward container 300. Surgical drainage tube 210, which can be a soft plastic tube exiting the patient's wound, connects drain 220 with valve port 500.

In many instances, drain 220 is constructed of a non-irritating material, such as soft silicone, Teflon, or other biocompatible materials. Drain 220 may be in any of a variety of shapes, including flat or tubular shapes. In some instances, drain 220 may be coated or otherwise treated with a pharmacological agent. Perforations or other surface features may cover all or a portion of drain 220. Similarly, drainage tube 210 can be constructed of biocompatible materials such as silicone. Container 300 is typically a flexible receptacle that provides uniform, stable, and gentle suction, and may be any of a variety of sizes, including a 100 cc volume container. Often, container 300 is constructed of transparent material that allows for visual inspection of the contents therein. One-way valve 400 is often an anti-reflux valve or other non-return valve that prevents regurgitation or backflow of fluids into the body.

In use, drain 220 and drainage tubing 210 are placed within a patient at a wound site during surgery, and are left there following surgery to allow fluid to be drawn from the site. Often, one or more devices may be left in the patient after the surgical procedure is completed. To activate device 100, the surgeon or operator typically removes plug 610 from venting port 600, and at least partially collapses container or bulb 300 by squeezing air from within container out through venting port 600. The operator then inserts plug 610 back into venting port 600, and releases the squeezing pressure on container 600, thereby generating a negative pressure within container 600. Negative pressure or suction from the container 300 is thus transmitted from container 300, through valve 400, valve port 500, drainage tube 210, to drain 220 which is at or near the patient's wound. Hence, drainage fluid is suctioned out of the patient and into container 300. After suction has been performed for the desired amount of time, the operator can unplug venting port 600 to allow container to return to atmospheric pressure. The fluid contents of container 300 can then be poured out through venting port into a receptacle for measurement or other further analysis. The operator then squeezes container 300 and replugs venting port 600 as described above to reestablish suction in device 100.

Interestingly, a survey of surgeons from all surgical sub-specialties at the University of California, San Francisco, including Interventional Radiology physicians who routinely place and remove closed suction drains, notes that nearly everyone presently removes such drains simply by un-plugging venting port 600, and then removing drainage tube 210 and drain 220 from the patient. When queried why they remove input passage 220 using this technique, nearly all responded that the reason was to remove drain 220 or drain terminus off suction, and that unplugging venting port 600 accomplishes this result.

As further discussed herein, by the aforementioned technique, physicians are unknowingly removing drain 220 while still to suction. The unexpected complication rate from removing drains on suction may be significant cause for concern. It is quite likely that a large component of the pain associated with drain removal is from traction to body tissues as drain 220 is removed.

The present invention may be preferred over currently used systems which are prone to pull body tissue from the patient along with the drain owing to the strength of the unwanted active suction. By preventing tissues from being ripped out of the body along with the drain, damage to the surgical site or unrelated surrounding tissues is avoided. Similarly, with the present invention there is a reduced pull on body tissues as the drain is removed, and therefore there is less pain to the patient. Studies have shown that drain removal is a very painful experience to the vast majority of patients.

FIGS. 2A-D illustrate a suction device 1100 according to one embodiment of the present invention. Device 1100 includes an input passage 1200 for receiving fluid from a site on or within a patient's body, a container 1300 for holding the drained fluid, and a reversible valve 1700 disposed between input passage 1200 and container 1300. When reversible valve 1700 is in an original configuration, as shown in FIGS. 2A and 2C, reversible valve 1700 provides unidirectional flow from input passage 1200 toward container 1300. When reversible valve 1700 is in a reversed configuration, as shown in FIGS. 2B and 2D, reversible valve 1700 provides fluid flow from container 1300 toward input passage 1200.

In some embodiments, reversible valve 1700 can include a one-way valve 1400 such as a Heimlich valve and a stent or tube 1710. In such embodiments, when reversible valve 1700 is in the original configuration depicted in FIGS. 2A and 2C, fluid flow from input passage 1200 toward container 1300 forces a seal 1410 of one-way valve 1400 to an open position and fluid flow from container 1300 toward input passage 1200 forces seal 1410 to a closed position. When reversible valve 1700 is in the reversed configuration depicted in FIGS. 2B and 2D, stent 1710 is partially advanced through seal 1410 to maintain seal 1410 in an open position.

In related embodiments, stent 1710 is a threaded rigid connector tube disposed through valve port 1500, and can be screwed or pushed in toward container 1300 bulb and across one-way valve 1400, thus forcing one-way valve 1400 open and providing a tubular continuity between container 1300 and input passage 1200. In certain instances, drain tube 1210 is allowed to lose suction because venting port 1600 is opened to the environment thus allowing container 1300 to return to atmospheric pressure. This continuity is also reversible, in that stent 1710 can be screwed or pulled back from one-way valve 1400, away from container 1300 bulb, thus allowing one-way valve 1400 to return to a competent state.

When input passage 1200 and container 1300 are in open fluid communication with one another, device 1100 can effectively act as a gravity, or passive, drainage system. In other words, drainage fluid from the wound can dribble into drain 1220, along drainage tube 1210, across the now stented or otherwise open, or in some cases bypassed, one-way valve 1400, and into container 1300. Surgeons may elect to take drain 1220 off suction for cyclic periods, if it is felt that the suction effect provided by container 1300 is in fact promoting drainage from the wound. Thus, the present invention also provides a design whereby an active or suction drain (e.g. FIGS. 2A and 2C) can be easily and reversibly converted to a simple gravity drainage (e.g. FIGS. 2B and 2D), as desired, and then returned to suction, as desired.

When one-way or Heimlich valve 1400 is stented, it is also possible to flush fluid such as liquid or air in a retrograde fashion from container 1300 across one-way valve 1400 and toward and into the patient. In some cases, container 1300 can be filled with a desired fluid, for example a radiographic contrast or a drug fluid via an open venting port 1600. Then after venting port 1600 is re-plugged, the operator can squeeze container 1300 to force air or the chosen fluid to be expelled retrograde across the now stented or otherwise bypassed one-way valve, along drainage tube 1210 and drain 1220, and into the patient. In some cases, the fluid can act to push away any tissue that may be intercalated within the interstices of the drain holes, crevices, free edges, or other features of drain 1220. It may be desirable to perform such a procedure prior to pulling drain 1220 out of the patient. Alternatively, radiographic contrast can serve to radiographically illuminate the location of drain 1220 within the patient.

The present invention allows structural changes to be made in device 1300 via reversible valve 1700 such that device 1300 remains in effect a closed system, without ever having to leave device 1100 open to the environment, or, to introduce a foreign body into the inside of the otherwise closed system defined by device 1100.

Figures 3A, 3B:
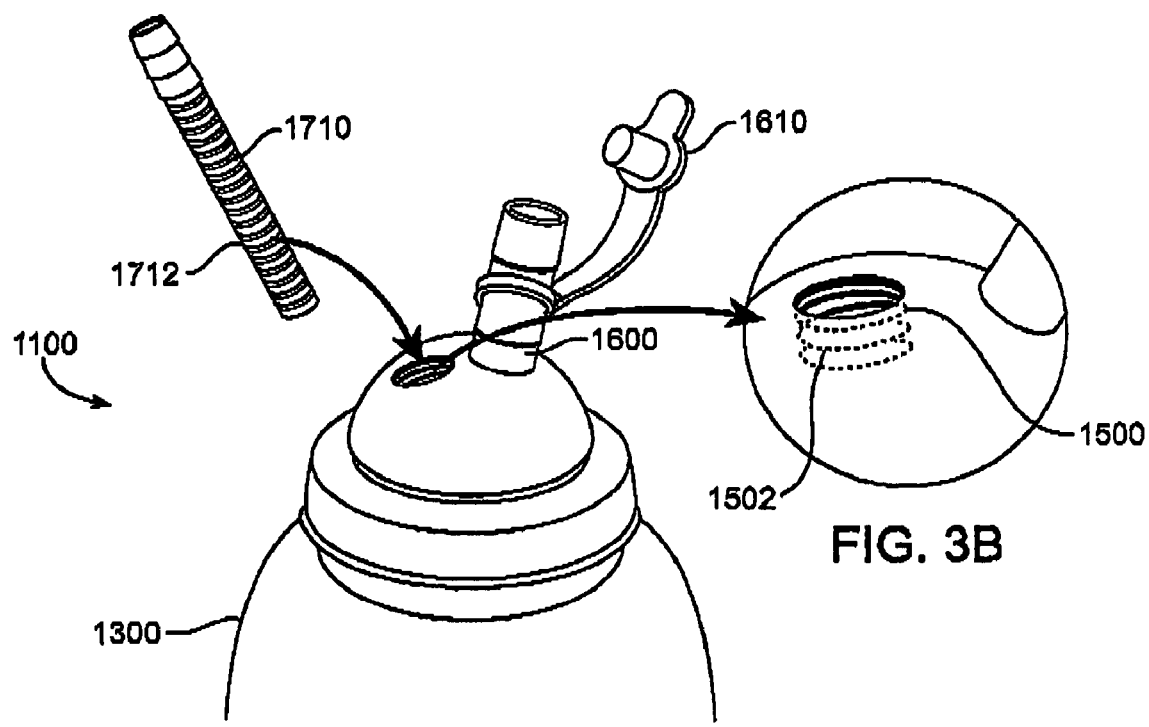
FIGS. 3A and 3B illustrate a wound drainage system according to one embodiment of the present invention.

FIGS. 3A and 31B provide additional views of suction device 1100. Stent 1710 includes a threaded section for engagement with valve port 1500, which also includes a threaded section 1502. Stent 1710 can be advanced toward container 1300 by rotating stent 1710 in one direction, and conversely, stent 1710 can be withdrawn away from container 1300 by rotating stent 1710 in the opposite direction.

FIGS. 4A and 4B illustrate a suction device 2100 according to one embodiment of the present invention. Device 2100 includes an input passage 2200 for receiving fluid from a site on or within a patient's body, a container 2300 for holding the drained fluid, and a reversible valve 2700 disposed between input passage 2200 and container 2300. When reversible valve 2700 is in an original configuration, as shown in FIG. 4A, reversible valve 2700 provides unidirectional flow from input passage 2200 toward container 2300. When reversible valve 2700 is in a reversed configuration, as shown in FIG. 4B, reversible valve 2700 provides fluid flow from container 2300 toward input passage 2200.

In some embodiments, reversible valve 2700 can include a one-way valve 2400 such as a Heimlich valve and a bypass 2730. In such embodiments, when reversible valve 2700 is in the original configuration depicted in FIG. 4A, fluid flow from input passage 2200 toward container 2300 forces a seal (not shown) of one-way valve 2400 to an open position and fluid flow from container 2300 toward input passage 2200 forces seal (not shown) to a closed position. Bypass 2730 is blocked, for example by valve port 2500, from providing fluid communication between container 2300 and input passage 2200. When reversible valve 2700 is in the reversed configuration depicted in FIG. 4B, bypass 2730 is unblocked and provides fluid communication between container 2300 and input passage 2200.

The present invention contemplates any of a variety of mechanisms or techniques for allowing the release of a negative vacuum pressure from the input passage, or otherwise equilibrating the pressure in the input passage to atmospheric pressure. For example, equilibration devices can be interposed between the patient and the one-way valve at many locations along the input passage. In some cases, this can involve coupling a stopcock element with the input passage. As the key of the stopcock is turned, air is allowed into the input passage to equalize the pressure therein to atmospheric pressure. In other cases, a connector can be spliced into the input passage. The connector may be unscrewed so that air is allowed to enter the input passage through an aperture such as a pinhole, thereby releasing the negative pressure in the input passage and equilibrating the input passage to atmospheric pressure. In still other cases, a pluggable hole may be disposed at any point along the input passage between the one-way valve and the patient, so that when the hole is unplugged, air is allowed to enter the input passage thereby equalizing the pressure inside the input passage with atmospheric pressure. In related cases, the suction bulb or container itself can be reconfigured to provide a means by which a one-way valve can be compromised when desired, so that if suction is released within the container, as is routinely done by unplugging a venting port, the loss of vacuum is transmitted through to the input passage.

Figure 5:
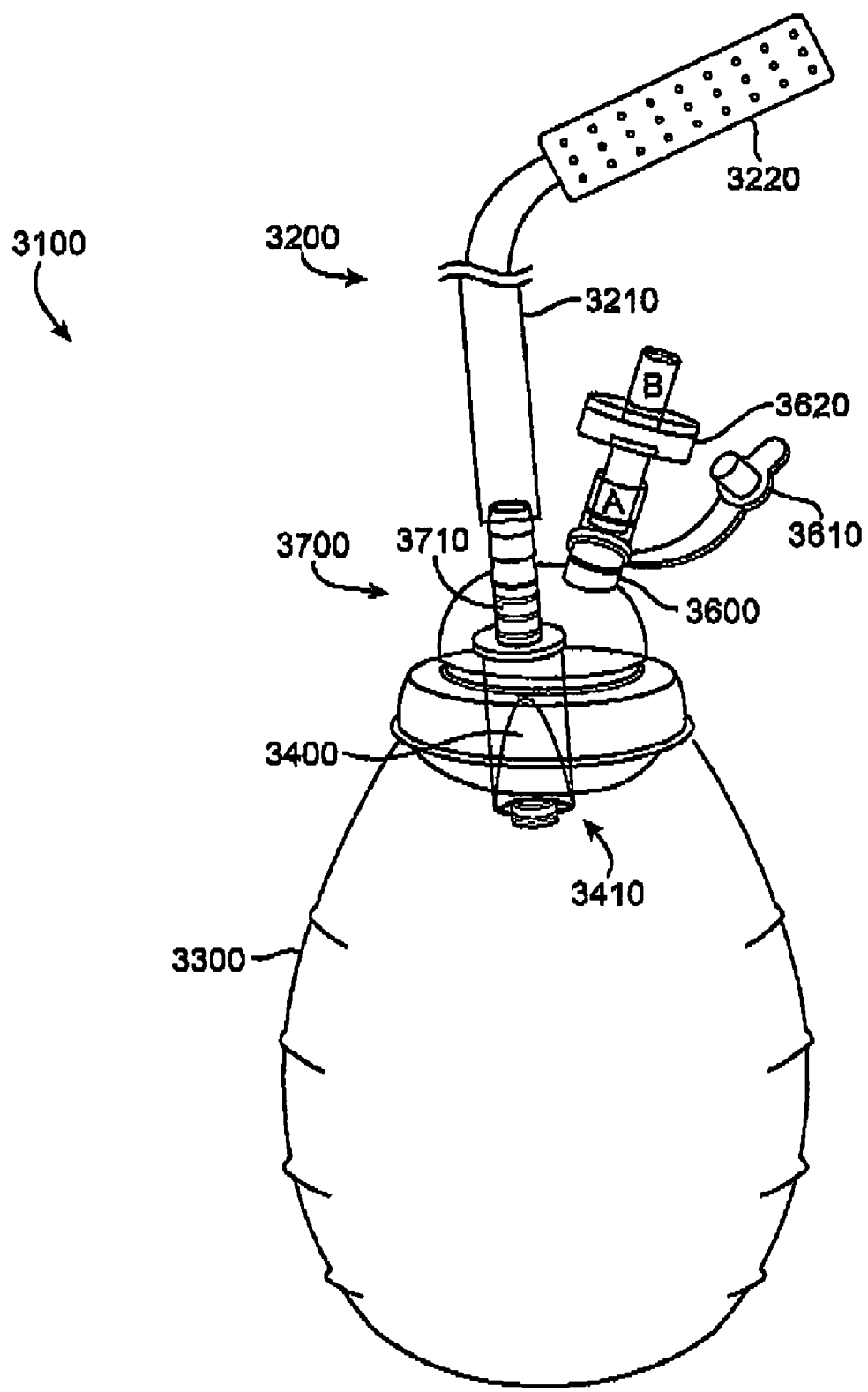
FIG. 5 illustrates a wound drainage system according to one embodiment of the present invention.

FIG. 5 illustrates a suction device 3100 according to one embodiment of the present invention. Device 3100 includes an input passage 3200 for receiving fluid from a site on or within a patient's body, a container 3300 for holding the drained fluid, and a reversible valve 3700 disposed between input passage 3200 and container 3300. When reversible valve 3700 is in an original configuration, similar to that shown in FIGS. 2A and 2C, reversible valve 3700 provides unidirectional flow from input passage 3200 toward container 3300. When reversible valve 3700 is in a reversed configuration, as shown here, reversible valve 3700 provides fluid flow from container 3300 toward input passage 3200.

In some embodiments, reversible valve 3700 can include a one-way valve 3400 such as a Heimlich valve and a stent or tube 3710. In such embodiments, when reversible valve 3700 is in the original configuration (not shown here), fluid flow from input passage 3200 toward container 3300 forces a seal 3410 of one-way valve 3400 to an open position and fluid flow from container 3300 toward input passage 3200 forces seal 3410 to a closed position. When reversible valve 1700 is in the reversed configuration as depicted here, stent 3710 is partially advanced through seal 3410 to maintain seal 3410 in an open position.

In related embodiments, stent 3710 is a rigid connector tube disposed through valve port 3500, and can be screwed or pushed in toward container 3300 bulb and across one-way valve 3400, thus forcing one-way valve 3400 open and providing a tubular continuity between container 3300 and input passage 3200. In certain instances, drain tube 3210 is allowed to lose suction because venting port 3600 is opened to the environment thus allowing container 3300 to return to atmospheric pressure. This continuity is also reversible, in that stent 3710 can be screwed or pulled back from one-way valve 3400, away from container 3300 bulb, thus allowing one-way valve 3400 to return to a competent state.

In known systems such as those shown in FIG. 1, as container 300 fills with fluid, eventually container 300 becomes so full that new drained fluid meets counter pressure in container 300. This is because venting port 600 is plugged, effectively creating a closed system. Displaced air in container 300, along with previously drained fluid, is put to pressure by the incoming fluid flow. Ultimately, no further fluid flows, as container 300 is already expanded to it's maximum volume. To allow for the increase in pressure due to the continuing influx of drainage fluid from the patient, it is typically necessary to unplug venting port 600, empty the contents of container 300, and replug venting port 600. Current wisdom dictates that simply unplugging a venting port 3600 in a device 3100 having a one-way valve 3400 will immediately convert device 3100 from active drainage to passive drainage. Yet as described elsewhere herein, the present inventors have discovered this not to be the case, as negative pressure often remains in the input passage.

Advantageously, the present invention allows for a true passive drainage system. With reference to FIG. 5, for example, when one-way valve 3400 is compromised, input passage 3200 and container 3300 are in open fluid communication with one another, and device 3100 can effectively act as a gravity, or passive, drainage system. In other words, drainage fluid from the wound can dribble into drain 3220, along drainage tube 3210, across the now stented or otherwise open, or in some cases bypassed, one-way valve 3400, and into container 3300. Thus, the present invention also provides a design whereby an active suction drain can be easily and reversibly converted to a simple passive gravity drainage as desired, and then returned to suction, as desired. In fact, some patients benefit from a treatment protocol that involves alternating cycles of active and passive drainage, and the present invention provides an approach that is well suited for such treatment.

In some embodiments, device 3100 shown in FIG. 5 may also include a vent 3620 coupled with container 3300, for example via venting port 3600. Vent 3620 can include a one-way valve, such as a diaphragm valve, that allows unidirectional fluid flow through a venting port 3600 out of container 3300. Often, vent 3620 includes a sensitive low pressure device, such that the one-way valve responds to very slight pressure gradients. The air flow direction through vent 3620 is from A to B, as depicted in FIG. 5. Advantageously, vent 3620 can prevent spillage from venting port 3600 while at the same time allowing air to be released therethrough, as opposed to the situation where venting port 3600 is simply unplugged. Similarly, vent 3620 can prevent contaminants from entering container 3300 in a direction from B to A across vent 3620 and ultimately the patient's wound, which could otherwise happen when venting port 3600 is simply left open. In this sense, the present invention provides a vented, sterile, passive drainage system that is closed to some extent but still allows venting while preventing contamination.

In some cases, device 3200 includes vent 3620 and an intact one-way valve 3400, in a configuration to apply active drainage to the wound. When container 3300 expands sufficiently, the operator can squeeze container 3300 to expel air through vent 3620. Air is prevented from returning into container 3300 via vent 3620, and suction is maintained. In this way, a surgeon can operate the bulb in a ratcheting fashion, expelling air via vent 3620 when needed, while still allowing fluid flow from input passage 3200 into container 3300.

In some embodiments, vent 3620 includes a screw-on cap, whose top surface is made of a synthetic mesh-like material that is sufficiently permeable to allow air to escape, but also acts sufficiently as a barrier to prevent spillage. In some embodiments, vent 3620 includes a Luer-lock cap, whose top surface is made of the synthetic mesh-like material. It can be screwed onto or otherwise affixed with venting port 3600 whenever gravity dependent drainage is desired. Alternatively, a bag could be coupled with container 3300. The bag could be small, made of extremely thin material, and could act as a low pressure receptacle for air as container 3600 is filled. In some embodiments, vent 3620 is fixed with container 3300. In other embodiments, vent 3620 can be detached and reattached from container 3300. Accordingly, the operator may decouple vent 3620 from container 3300, empty the contents of container 3300, and recouple vent 3620 to container 3300. Vent 3620 can be any of a variety of one-way valves, such as a diaphragm valve or a Heimlich valve. In some embodiments, vent 3620 can be a check valve from a infusion set (REF 2426-0500, Alaris Medical Systems, San Diego, Calif.).

Figure 6:
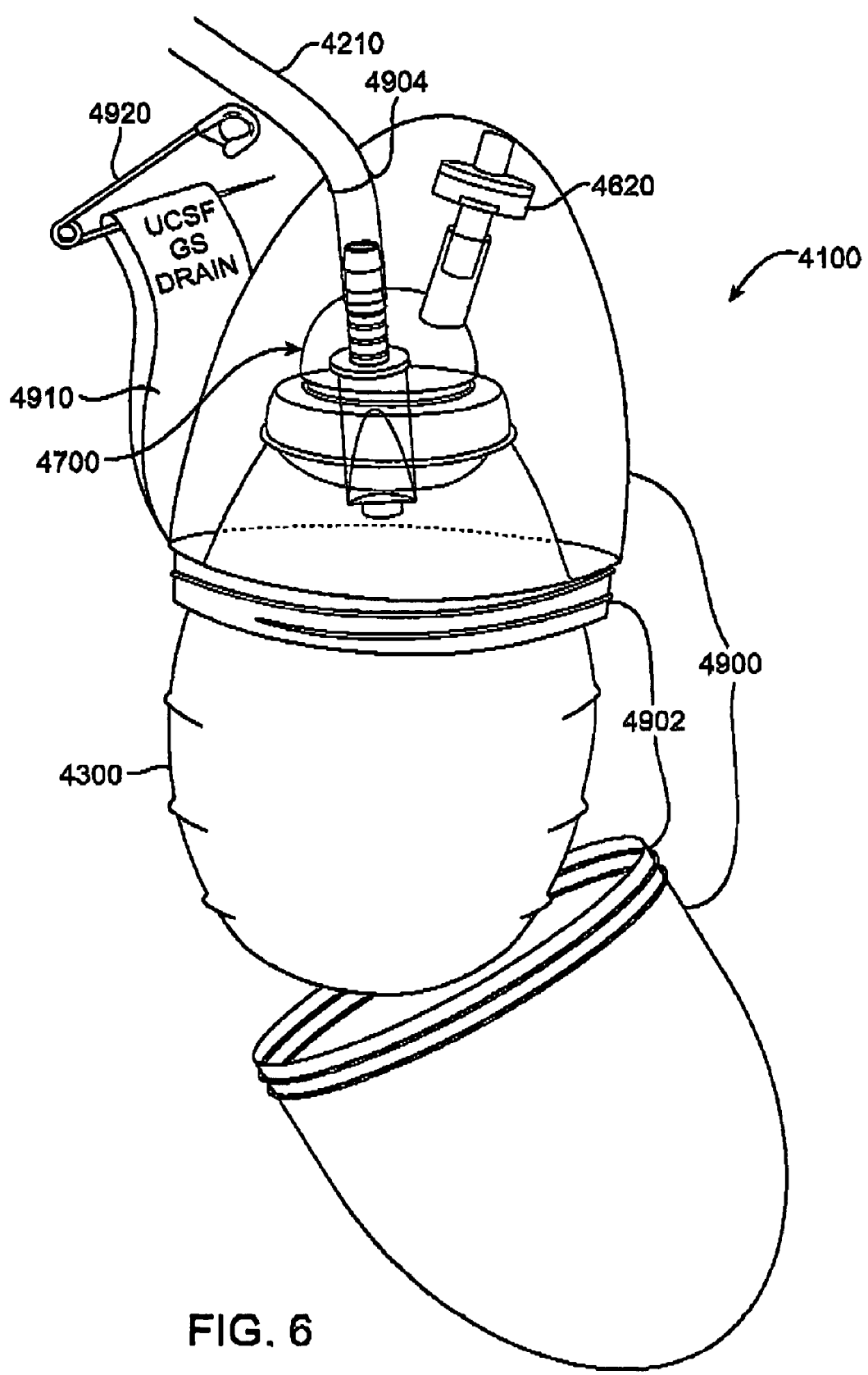
FIG. 6 illustrates a wound drainage system according to one embodiment of the present invention.

FIG. 6 illustrates drainage device 4100 according to one embodiment of the present invention. Here, device 100 includes a shell 4900 configured to house reversible valve 4700, vent 4620. In the embodiment depicted here, shell 4900 is constructed of two pieces, each including a threaded section 4902 whereby they may be coupled together. Shell 4900 also includes an aperture 4904 for receiving drainage tube 4210 therethrough. The diameter of aperture 4904 may be sized slightly larger than the diameter of drainage tube 4210, so that air escaping from vent 4620 can also escape from shell 4900. Shell 4900 may also be coupled with a loop or connector 4910 for fastening device 4100 with the patient's clothing with pin 4920. By fastening device 4100 with the patient's clothing, accidental removal of drainage tubing 4210 from the patient's body can be prevented.

Advantageously, shell 4100 operates to protect container 4300 from unintentional collapse, which may result if the patient accidentally bumps against or otherwise deforms container 4300. In some cases, this may cause excessive or otherwise unwanted fluid flow out of container 4300 through vent 4620 without incurring an equalizing influx from drainage tube 4210, thus putting the system to suction. This can be a negative outcome where the treatment protocol requires uninterrupted passive drainage. In related cases, this may cause unwanted fluid flow of fluid from container 4300, through stented reversible valve 4700 and drainage tube 4210, and into the patient.

In many of the embodiments described herein, one way valves of the present invention include Heimlich valves having a plurality of flutter leaflets that are biased toward each other in a coapting fashion to form a releasable seal. Typically, a Heimlich valve includes a bi-leaflet valve constructed of rubber tubing, is compressed at one end to form leaflets that control unidirectional flow, and is encased in a transparent plastic chamber with tapered ends. An input end of the casing can be attached to a drainage tube and the output end can be coupled with a receiving container. If desired, the output end can be coupled with a suction source. Other one-way valves described herein include diaphragm valves. However, it is appreciated that the one-way valves of the present invention may be exemplified by any of a variety of valve types or devices for regulating the flow of gases, liquids, or loose materials through apertures by selectively opening, closing or obstructing ports or passageways. As such, valves according to the present invention include, but should not be limited to, check valves such as single-disc swing valves, double disc swing valves, wafer valves, lift-check valves, silent valves, center guide valves, ball-check valves, and cone-check valves. Valves of the present invention may also include air valves, back flow preventers, ball valves, butterfly valves, control valves, dispensing valves, diverter valves, emergency shut-off valves, gas pressure regulators, gas valves, gate valves, globe valves, hydraulic regulators, hydraulic valves, mixing valves, needle valves, pinch valves, plug valves, pressure regulators, pressure relief valves, safety shut-off valves, servo valves, solenoid valves, tapping valves, thermally actuated valves, valve circuits, and water valves.

Various experiments were performed to determine the extent to which release of vacuum from a drain bulb leads to release of vacuum at a drain tube end. Further experiments were performed to quantify maximal negative pressure capacities of two commonly used suction drainage bulbs.

In a first experiment, a pressure transducer (Bio-Tek, DPM-IB, USA) was applied to the drain tubing inlet of 5 identical Davol (Jackson Pratt) 100 cc silicone closed wound suction evacuator bulbs (BARD, USA). Each bulb was placed to complete bulb-suction. Negative pressures were recorded before, during, and after release of bulb-suction. To quantify suction magnitude at different bulb volumes, values were recorded with the bulb filled with 25, 50, 75, and 100 cc of saline. Each trial was repeated 5 times. Values were recorded and statistical analysis was performed with the Student's t-Test.

Measured suction values ranged from negative 80 to negative 170 mm Hg, dependent upon the degree of "squeeze" applied to the bulb. Suction recorded at various bulb volumes varied minimally (<2%). After the bulb suction was released negative pressure persisted, yet the net pressure changed by only +4.5 mm Hg for each bulb. No further loss of suction was observed during subsequent observation (2 hours). Mean suction values with the bulb filled with 25, 50, 75, and 100 cc saline were −58 mmHg, −33 mmHg, −28 mmHg, and −27, respectively.

In a second experiment, a pressure transducer was used to compare suction characteristics of a Jackson-Pratt Davol 100 cc Closed Wound Suction Evacuator Reservoir with a Davol 400 cc Reliavac Evacuator Reservoir. Both commonly used closed-system bulb suction drains were placed to suction and connected to a Bio-Tek digital pressure transducer. Static suction from the drain was measured continuously before, during, and after unplugging the drainage bulb. Negative pressures were recorded after filling each bulb (25%, 50%, 75%, and 95% bulb capacity). Measurements were repeated after squeezing the bulb from one side ("bottom-up"), two opposite sides ("flat"), and four sides ("four-point cross").

It was observed that the recorded maximal suction varied according to how the drain was compressed prior to plugging. Maximal suction was achieved when the circular bulb was compressed from four points (12, 3, 6, and 9 O'clock), versus only one or two points. At all reservoir volumes, static suction did not decrease with unplugging of the bulb. The results of the second experiment are summarized in Table 1. Increased positive pressure within the bulb is not necessarily transmitted across the one-way valve toward the drain end. Negative pressures varied according to how full the bulb reservoir was, and how the bulb was squeezed. The bulb wall thickness and shape have an impact on net pressures.

TABLE 1

| Different squeezing techniques: | | Davol JP Bulb (100 cc) Mean Static Suction (mmHg) | Davol Reliavac (400 cc) Evacuator Mean Static Suction (mmHg) |
|---|---|---|---|
| "Bottom-Up" | | | |
| Reservoir empty/plugged | | 19 | 28 |
| Reservoir empty/unplugged | | 18 | 24 |
| Labelled reservoir capacity: | 25% full | 19 | 23 |
| | 50% full | 21 | 30 |
| | 75% full | 22 | 29 |
| | 95% full | 35 | 18 |
| "Flat" | | | |
| Reservoir empty/plugged | | 82 | 28 |
| Reservoir empty/unplugged | | 79 | 27 |
| Labelled reservoir capacity: | 25% full | 45 | 38 |
| | 50% full | 23 | 26 |
| | 75% full | 20 | 18 |
| | 95% full | 19 | 18 |
| "4-Point" | | | |
| Reservoir empty/plugged | | 165 | 77 |
| Reservoir empty/unplugged | | 162 | 75 |
| Labelled reservoir capacity: | 25% full | 98 | 81 |
| | 50% full | 43 | 45 |
| | 75% full | 25 | 39 |
| | 95% full | 25 | 23 |

Hence, the present inventors have discovered that the closed suction wound drain element maintained steady and constant negative pressure long after the bulb suction was released. This was due to a one-way valve located on the bulb where the drain tube connects, which was designed to prevent fluid reflux. Deformation of the elastic walls of the drainage tubing serve as the persistent source of suction. To release the drain element from suction, entry of air into drain tubing is often required. Release of suction and efficient gravity dependent drainage are precluded by the presence of the one-way valve in presently available drains. Thus, when using current evacuator bulbs, it may not be likely that unplugging the venting port immediately leads to release of drain suction, or to passive gravity-dependant drainage into the bulb.

The results of these experiments contradict the common belief that release of suction within the bulb also releases suction from the drain end within the body. In this sense, although surgeons may believe they are removing the drain from the patient when the drain is off suction, in fact the drain is still to suction. If negative pressure within the bulb is lost, for example by unplugging the first port to allow air into the bulb, negative pressure distal to the one-way valve is maintained, as the air that has been allowed to enter the lumen of the bulb via the venting port cannot cross the one-way valve toward the patient. Hence, the surgical drainage tube connected to the bulb at the valve port remains effectively to suction.

The closed suction bulb device of the present invention, however, provide a means by which the one-way valve can be made reversibly patent, and a means by which the bulb can serve as an efficient collection reservoir for non-suction, gravity dependent flow, when desired. The present invention eliminates a flaw in current closed-system suction wound drains, and permits reversible suction versus gravity dependant closed-system drainage.

The present inventors have observed that drain suction bulbs are capable of generating varying degrees of suction, for example based on how and to what degree they are squeezed free of air before being sealed by closing the venting port. At least some of these observations are provided in Table 1. Other factors that can affect how much suction is created in the bulb include the thickness and shape of the bulb, as well as the composition and construction of the bulb material itself. In some cases, the suction in the bulb is determined by the magnitude of the bias that the bulb manifests toward returning to it's original configuration. Advantageously, by optimizing the usage and bulb characteristic parameters, it is possible to provide customized or otherwise controlled suction amounts to a wound site. This can provide substantial benefit to a patient because insufficient drainage may not adequately drain the wound, and an excessive vacuum may damage the tissue or prevent appropriate healing of the wound, for example by not allowing an anastomosis to heal correctly.

One factor that determines the degree of suction generated by a squeezed bulb is the number of folded edges created in the bulb. For example, a simple squeeze of a bulb generates two folded edges. In some bulbs, this roughly corresponds to about 60 to about 80 mm Hg. However, one squeezes the same bulb using two hands such that four folded edges are generated, then a higher degree of suction can be generated. In such bulbs, this roughly corresponds to about 180 mm Hg. Approximately the same amount of air is displaced, but the four-folded bulb configuration has a greater bias toward returning to the original configuration than does the two-fold bulb configuration.

Accordingly, the present invention includes drain suction bulbs having surface markings to guide, instruct, or otherwise assist the user in applying certain squeezing techniques to the bulb in order to optimize the pressure created by the bulb to the particular task for which the bulb is being used. By positioning their fingers on the bulb in certain ways, or by squeezing the bulb in a certain fashion, the user can achieve varying documented or otherwise standardized degrees of suction generated by the bulb. In some instances, a squeezing design can be imprinted onto the bulb, with a depiction of where to pinch or otherwise how to create pinch points or crease points in the bulb, to generate the desired degree of suction. When maximal suction is desired, a pictogram can detail how and where to pinch or squeeze the bulb, to generate maximal suction. Moderate or minimal suction, or any degree of suction therebetween, can likewise be instructed pictographically. Such surface markings include numbers, letters, symbols, flattened areas, ridges, textured areas, or other surface features that can be seen or felt from the outside of the bulb. Often, such surface features will be on the outer wall of the bulb.

Squeeze bulb folding configurations include, but should not be limited to, the examples shown in FIGS. 7A-7F. A bottom-up folding configuration is depicted in FIG. 7A. By pressing upward on the bottom of container 5300, a circumferential crease is created. To clarify the illustration, a cap 5800 is shown on top of container 5300. A flat folding configuration is depicted in FIG. 7B. By pressing at finger points or traction points 5330, two creases 5340 are created in container 5300 (e.g. at 3 and 9 O'clock positions). A taco folding configuration is depicted in FIG. 7C. By first pressing at finger points 5330, and then pressing at finger points 5332, four creases 5340 are created in container 5300 (e.g. 11 and 1 O'clock positions, and two creases at 6 O'clock positions). A triad folding configuration is depicted in FIG. 7D. By pressing at finger points 5330, three creases 5340 are created in container 5330 (e.g. at 12, 4, and 8 O'clock positions). A cross or clover folding configuration is depicted in FIG. 7E. By pressing at finger points 5330, which may require two hands or the aid of an assistant, four creases are created in container 5300 (e.g. at 3, 6, 9, and 12 O'clock positions). FIG. 7F shows a side view of device 5100 corresponding to the flat folding configuration of FIG. 7B. Opposing sides of container 5300 include surface markings 5350, and when an operator applies pressure to container 5300 along markings 5350, creases are created along crease lines 5340. The present invention also provides devices or fixtures that can be contacted with the bulb to apply a squeezing pressure to the bulb in predetermined standardized ways, so that near exact degrees of suction can be generated as desired. For example, the present invention provides tools for squeezing the bulb so as to introduce 3, 4, or 5 folds in the bulb wall.

Another factor that determines the degree of suction generated by a squeezed bulb is the thickness of the bulb wall. In some cases, select sections of the bulb wall will vary in thickness from other bulb sections. The degree of suction generated by a squeezed bulb can depend on the thickness of the bulb wall where the crease lines are created. For example, a crease in the bulb along a thicker area may create more suction than a crease in the bulb along a thinner area. The bulb may also include surface markings for squeezing the bulb in certain areas so as to take advantage of these bulb wall thickness characteristics to generate the desired amount of suction in the bulb.

Yet another factor that can determine the degree of suction generated by a squeezed bulb is the shape of the bulb when the bulb is at rest, or without vacuum. Although many bulbs currently used are oblong or football-shaped, the present invention contemplates any of a variety of regular and irregular bulb shapes, so long as the shape is effective for optimizing the desired suction characteristics. For example, the bulb shape may be spherical, teardrop shaped, or tubular. The shape may also be more squat or even more elongated than the standard bulbs discussed herein. In some case, the bulb shape may include a combination of subshapes. For example, one end of the bulb may be spherical and the other end may be rectangular or pyramidal. The bulb may also include surface markings for squeezing the bulb in certain areas so as to take advantage of these bulb shape characteristics to generate the desired amount of suction in the bulb.

Still another factor that can determine the degree of suction generated by a squeezed bulb is the composition of the bulb material itself. In some cases, the bulb may be of unilaminar construction. For example, the bulb may be made entirely of silicone or a biocompatible or otherwise suitable material. The bulb may also be of multilaminar construction, such as then the interior of the bulb is constructed of silicone, and the outside is constructed of some other material. It is appreciated that certain areas of the bulb may be unilaminar, and other areas may be multilaminar. In a related case, the elasticity of the material used to construct the bulb may be varied in order to achieve a desired suction profile. Various elasticity profiles may be achieved by introducing dopants or otherwise integrating elasticity enhancers or inhibitors into the bulb material. For example, more elastic materials may confer the bulb with a lower suction profile, whereas less elastic materials may confer the bulb with a higher suction profile. By varying the elasticity of certain portions of the bulb, it is possible to vary the amount of stored or potential energy created in the bulb as it is squeezed, and hence the propensity of the bulb to return to its original shape. Any of the bulb composition features discussed herein may correspond to crease points in the bulb so as to achieve a certain amount of suction in squeezed bulb. In some cases, the bulb composition material or other features may be selected so as to provide a desired time-course suction profile. For example, the bulb may be constructed so as to initially provide a high suction which then slowly diminishes over time. Likewise, the bulb may be constructed to provide a continuous and constant pressure profile over time. The bulb may also include surface markings for squeezing the bulb in certain areas so as to take advantage of these bulb composition characteristics to generate the desired amount of suction in the bulb.

Based on the foregoing, the present invention provides methods of making and using vacuum bulbs so as to optimize suction characteristics of the bulb for a particular task such as facilitating drainage of a wound. Toward this end, the present invention provides vacuum bulbs that deliver consistent and reproducible amounts of suction during use. Any of the factors that affect suction discussed herein, for example bulb shape or thickness, can be combined or otherwise permutated so as to manufacture or use the bulb optimally for the chosen task.

The above provides a full and complete disclosure of certain embodiments of the present invention for purposes of clarity and understanding. However, it will be appreciated that various modifications, alternate constructions, and equivalents may be employed as desired. Therefore, the above description and illustrations should not be construed as limiting the invention, which is defined by the appended claims.

What is claimed is:

1. A drainage device for draining a wound fluid from a patient, the device comprising:
    an input passage for receiving the wound fluid from a site on or within the patient's body;
    a container for holding the fluid; and
    a reversible valve disposed between and coupled with the input passage and the container, wherein the reversible valve in an original configuration provides unidirectional fluid flow from the input passage toward the container when coupled with the input passage and the container, and in a reversed configuration provides fluid flow from the container toward the input passage when coupled with the input passage and the container,
    wherein the reversible valve comprises a one-way Heimlich valve in cooperative association with a stent such that when the reversible valve is in the original configuration, fluid flow from the input passage toward the container forces a seal of the Heimlich valve to an open position and fluid flow from the container toward the input passage forces the seal of the Heimlich valve to a closed position, and when the reversible valve is in the reversed configuration, the stent is disposed through the seal to maintain the seal in the open position.

2. The drainage device of claim 1, further comprising a sealable port coupled with the container.

3. The drainage device of claim 1, further comprising a vent coupled with the container, wherein the vent provides unidirectional fluid flow through a venting port out of the container.

4. The drainage device of claim 3, wherein the vent comprises a diaphragm valve or a Heimlich valve.

5. The drainage device of claim 3, further comprising a shell that houses the container, the shell comprising an aperture for receiving a drainage tube of the input passage therethrough.

6. A drainage device for draining a wound fluid from a patient, the device comprising:
    an input passage for receiving the wound fluid from a site on or within the patient's body;
    a container for holding the fluid; and
    a reversible valve disposed between and coupled with the input passage and the container, wherein the reversible valve in an original configuration provides unidirectional fluid flow from the input passage toward the container when coupled with the input passage and the container, and in a reversed configuration provides fluid flow from the container toward the input passage when coupled with the input passage and the container, wherein the container comprises a threaded section, wherein the reversible valve comprises a one-way Heimlich valve in cooperative association with a stent, and wherein the stent comprises a threaded section that engages the threaded section of the container.

7. The drainage device of claim 6, further comprising a sealable port coupled with the container.

8. The drainage device of claim 6, further comprising a vent coupled with the container, wherein the vent provides unidirectional fluid flow through a venting port out of the container.

9. The drainage device of claim 8, wherein the vent comprises a diaphragm valve or a Heimlich valve.

10. The drainage device of claim 8, further comprising a shell that houses the container, the shell comprising an aperture for receiving a drainage tube of the input passage therethrough.

* * * * *